US007037500B1

(12) United States Patent
Silverstein et al.

(10) Patent No.: US 7,037,500 B1
(45) Date of Patent: May 2, 2006

(54) METHOD FOR USING PHAGOCYTIC PARTICLES AND ATP RECEPTORS TO DELIVER ANTIGENS TO MHC CLASS I RECEPTORS TO INDUCE IMMUNITY AGAINST MICROBIAL PATHOGENS OR TUMORS OR TO SUPPRESS IMMUNITY

(75) Inventors: Samuel C. Silverstein, New York, NY (US); John D. Loike, Jamaica, NY (US); Francesco DiVirgilio, Polverara (IT)

(73) Assignee: The Trustees of Columbia University in the City of New York, New York, NY (US)

( * ) Notice: Subject to any disclaimer, the term of this patent is extended or adjusted under 35 U.S.C. 154(b) by 90 days.

(21) Appl. No.: 09/658,698

(22) Filed: Sep. 8, 2000

(51) Int. Cl.
*A61K 5/10* (2006.01)
*A61M 36/14* (2006.01)

(52) U.S. Cl. ............... 424/184.1; 424/450; 424/278.1; 424/93.73; 428/402.2

(58) Field of Classification Search ............. 424/491, 424/450, 184.1, 278.1, 93.73; 428/402.2; 530/300, 359, 395
See application file for complete search history.

(56) References Cited

OTHER PUBLICATIONS

Grufman, P and K arre. Eur. J. Immunol. (2000) 30:1088-1093.*
Ia Sala, A et al. J. Immunol. (2001) 166:1611-1617.*
Ia Sala, A et al. Blood (2002) 99(5):1715-1722.*
Buckner, F.S., et al. (1997) "Trypanosoma cruzi infection does not impair major histocompatibility complex class I presentation of antigen to cytotoxic T lymphocytes", *Eur J Immunol.*, 27(10):2541-2548 (Exhibit I).
Coutinho-Silva, R., et al. (1999) "P2Z/P2X7 receptor-dependent apoptosis of dendritic cells", *Am. J. Physiol.*, 276(5):C1139-C1147 (Exhibit 2).
Fratazzi, C., et al. (1997) "Programmed cell death of Mycobacterium avium serovar 4-infected human macrophages prevents the mycobacteria from spreading and induces mycobacterial growth inhibition by freshly added, uninfected macrophages", *J. Immunol.*, 158(9):4320-4327 (Exhibit 3).
Lin, W.C., et al. (1990) "Bacterial lacZ gene as a highly sensitive marker to detect micrometastasis formation during tumor progression", *Cancer Res.*, 50(9):2808-2817 (Exhibit 4).
MacKenzie, A.B., et al. (1999) "Functional and molecular diversity of purinergic ion channel receptors", *Ann. N.Y. Acad. Sci.*, 868:716-729 (Exhibit 5).
Mellman, I., et al. (1998) "Antigen processing for amateurs and professionals", *Trends in Cell Biol.*, 8(6):231-237 (Exhibit 6).
Mutini, C., et al. (1999) "Mouse dendritic cells express the P2X7 purinergic receptor: characterization and possible participation in antigen presentation", *J. Immunol.*, 163(4):1958-1965 (Exhibit 7).
Steinberg, T.H., et al. (1987) "ATP4- permeabilizes the plasma membrane of mouse macrophages to fluorescent dyes", *J. Biol. Chem.*, 262(18):8884-8888 (Exhibit 8).
Zambon, A., et al. (1994) "Role of extracellular ATP in cell-mediated cytotoxicity: a study with ATP-sensitive and ATP-resistant macrophages", *Cell Immunol.*, 156(2):458-467 (Exhibit 9).
Koppelman, B., et al., Evidence for peptide transport across microsomal membranes. Proceedings of the National Academy of Sciences, USA, May 1992, vol. 89, pp. 3908-3912 (Exhibit 1).
Ben-Shahar, S., et al., Production of Specific Major Histocompatibility Complex Class-I-Restricted Epitope by Ubiquitin-Dependent Degradation of Modified Ovalbumin in Lymphocyte Lysate. The Journal of Biological Chemistry, Aug. 22, 1997, vol. 272, No. 34, pp. 21060-21066 (Exhibit 2); and.
Thomas, C., et al., Human Immunodeficiency Virus-1 env Impairs Fcgamma Receptor Mediated Phagocytosis Via a Cyclic Adenosine Monophosphate-Dependent Mechanism. Blood. Nov. 1, 1997, vol. 90, No. 9, pp. 3760-3765 (Exhibit 3).

* cited by examiner

*Primary Examiner*—Christina Chan
*Assistant Examiner*—F. Pierre VanderVegt
(74) *Attorney, Agent, or Firm*—John P. White, Esq.; Cooper & Dunham LLP

(57) ABSTRACT

This invention provides methods of delivering an antigen to an Class I or Class II MHC receptors to induce immunity against the antigen in a subject having a disease. This invention also provides methods of delivering an antigen to an Class II or class I MHC receptor to supress immunity against the antigen in a subject having a disease.

16 Claims, 5 Drawing Sheets

LY Flourescence image    Phase image 24 h incubation with LY E(IgG)

FIGURE 4B
Fig 1b. J774 cell that have ingested IgGrRBCg +LY

SEQUENCE LISTING

<160> NUMBER OF SEQ ID NOS: 24

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:short
      peptide

<400> SEQUENCE: 1

Pro Pro Asn Lys
 1

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence:Synthetic
      primers

<400> SEQUENCE: 2
cgcggatcca tgagcgataa aattattcac c                                   31

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:Synthetic
      primers

<400> SEQUENCE: 3
gcacggaccg caccactctg c                                              21

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:Synthetic
      primers

<400> SEQUENCE: 4
gtgcggtccg tgcaaaatga tc                                             22

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence:Synthetic
      primers

<400> SEQUENCE: 5
ccggaattcc tacaggttag cgtcgagg                                       28

<210> SEQ ID NO 6
<211> LENGTH: 48
<212> TYPE: DNA
<213> ORGANISM: Artificial Sequence
<220> FEATURE:
<223> OTHER INFORMATION: Description of Artificial Sequence:Synthetic
      primers -continued

```
<400> SEQUENCE: 6
gtgtgcggtc cgttagatgc tttatttcaa ggtgttccac caaacaag           48

<210> SEQ ID NO 7
<211> LENGTH: 63
<212> TYPE: DNA
<213> ORGANISM: Artificial Sequence
<220> FEATURE:
<223> OTHER INFORMATION: Description of Artificial Sequence:Synthetic
      primers

<400> SEQUENCE: 7
tatgcacgga ccgtgatcac gtggatgact aacccaaaca tcgtagatac tcttgtttgg   60
tgg                                                                  63

<210> SEQ ID NO 8
<211> LENGTH: 48
<212> TYPE: DNA
<213> ORGANISM: Artificial Sequence
<220> FEATURE:
<223> OTHER INFORMATION: Description of Artificial Sequence:Synthetic
      primers

<400> SEQUENCE: 8
gtgtgcggtc cgttaaagca aaggttatg aaccatgtta acagtggt             48

<210> SEQ ID NO 9
<211> LENGTH: 63
<212> TYPE: DNA
<213> ORGANISM: Artificial Sequence
<220> FEATURE:
<223> OTHER INFORMATION: Description of Artificial Sequence:Synthetic
      primers

<400> SEQUENCE: 9
tatgcacgga ccgtgaaagg tttgtaattg ttgggttaac attaattgac aaccactgtt   60
aac                                                                  63

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence:Synthetic
      primers

<400> SEQUENCE: 10
gtggtgtggg gtcccgcttt atttcaaggt gttcc                          35

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence:Synthetic
      primers

<400> SEQUENCE: 11
gtggtgtggg gtccctttca aggtgttcca ccaaac                         36

<210> SEQ ID NO 12
<211> LENGTH: 35
<212> TYPE: DNA
<213> ORGANISM: Artificial Sequence
<220> FEATURE:
```

```
<223> OTHER INFORMATION: Description of Artificial Sequence:Synthetic
      primers

<400> SEQUENCE: 12
gtggtgtggg gtcccggtgt tccaccaaac aagag                              35

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence:Synthetic
      primers

<400> SEQUENCE: 13
gtggtgtggg gtcccccacc aaacaagagt atctac                             36

<210> SEQ ID NO 14
<211> LENGTH: 38
<212> TYPE: DNA
<213> ORGANISM: Artificial Sequence
<220> FEATURE:
<223> OTHER INFORMATION: Description of Artificial Sequence:Synthetic
      primers

<400> SEQUENCE: 14
gtggtgtggg gtcccaacaa gagtatctac gatgtttg                           38

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence:Synthetic
      primers

<400> SEQUENCE: 15
gtgtatgcaa ggaccttgtg gatgactaac ccaaacatc                          39

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence:Synthetic
      primers

<400> SEQUENCE: 16
gtgtatgcaa ggaccttgac taacccaaac atcgtagata c                       41

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence:Synthetic
      primers

<400> SEQUENCE: 17
gtgtatgcaa ggaccttgcc aaacatcgta gatactcttg                         40

<210> SEQ ID NO 18
<211> LENGTH: 38
<212> TYPE: DNA
<213> ORGANISM: Artificial Sequence
<220> FEATURE:
<223> OTHER INFORMATION: Description of Artificial Sequence:Synthetic
``` primers

<400> SEQUENCE: 18
gtgtatgcaa ggaccttgat cgtagatact cttgtttg                              38

<210> SEQ ID NO 19
<211> LENGTH: 39
<212> TYPE: DNA
<213> ORGANISM: Artificial Sequence
<220> FEATURE:
<223> OTHER INFORMATION: Description of Artificial Sequence:Synthetic
      primers

<400> SEQUENCE: 19
gtgtatgcaa ggaccttgga tactcttgtt tggtggaac                             39

<210> SEQ ID NO 20
<211> LENGTH: 22
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 20

Leu Asp Ala Leu Phe Gln Gly Val Pro Pro Asn Lys Ser Ile Tyr Asp
 1               5                  10                  15

Val Trp Val Ser His Pro
            20

<210> SEQ ID NO 21
<211> LENGTH: 22
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 21

Leu Asp Ala Leu Phe Gln Gly Val Ala Ala Asn Lys Ser Ile Tyr Asp
 1               5                  10                  15

Val Trp Val Ser His Pro
            20

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 22

Cys Phe Gln Gly Val Pro Pro Asn Lys Ser Ile Tyr Asp Val
 1               5                  10

<210> SEQ ID NO 23
<211> LENGTH: 22
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 23

Leu Lys Gln Lys Val Met Asn His Val Asn Ser Gly Cys Gln Leu Met

```
                1               5              10              15
Leu Thr Gln Gln Leu Gln
                                20

<210> SEQ ID NO 24
<211> LENGTH: 22
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 24

Ala Val Glu Ala Ala Arg Gln Ile Glu Arg Glu Ala Gln Gln Gln Gln
 1               5                  10                  15

His Leu Tyr Arg Val Asn
            20
```

METHOD FOR USING PHAGOCYTIC PARTICLES AND ATP RECEPTORS TO DELIVER ANTIGENS TO MHC CLASS I RECEPTORS TO INDUCE IMMUNITY AGAINST MICROBIAL PATHOGENS OR TUMORS OR TO SUPPRESS IMMUNITY

Preliminary work for the invention disclosed was herein made in the course of work under NIH Grant No. AI 20516. Accordingly, the U.S. Government has certain rights in this invention.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

To initiate an adaptive immune response, antigen presenting cells (APCs) must process "foreign" proteins into peptides. These peptides associate with MHC proteins which transport these peptides to the APCs' plasma membrane where they are recognized in the context of MHC proteins by helper and cytotoxic T-cell precursors. Helper T-lymphocyte precursors recognize peptide in association with Class II MHC proteins while cytotoxic T-lymphocyte (CTL) precursors recognize peptide in association with Class I MHC proteins.

The major types of APC's (mononuclear phagocytes and dendritic cells) express plasma membrane receptors for $ATP^{4-}$ (1,2,3). These receptors are called $P2X_7$ receptors. Binding of $ATP^{4-}$ to $P2X_7$ receptors opens a "pore" in the plasma membranes of macrophages (4), and of dendritic cells (3,5) that allows molecules of up to ~900 daltons M.W. into the cytoplasm of these cells without killing the cells. The $ATP^{4-}$-activated pore of macrophages was first identified by applicants. The $P2X_7$ receptor is formed by the association of multiple protein subunits each 595 aa long.

At neutral pH and in the presence of physiological salts most of the ATP in extracellular fluids is complexed with divalent cations, primarily $Mg^{2+}$ and $Ca^{2+}$. Under these conditions, the equilibrium between $MgATP^{2-}/CaATP^{2-}$ and $ATP^{4-}$ strongly favors $MgATP^{2-}/CaATP^{2-}$. Consequently, $[MgATP^{2-}/CaATP^{2-}]$ in excess of 3 mM are required to achieve an $[ATP^{4-}]$ of >130 μM, the $[ATP^{4-}]$ needed to induce pore formation by $P2X_7$ receptors (4). [ATP]>3 mM are rarely if ever found in extracellular fluids under physiological conditions. However, apoptotic cells contain >5 mM ATP (6).

Scavenger receptors present on the plasma membranes of APCs promote the phagocytosis of apoptotic cells. Following their ingestion, apoptotic cells are sequestered and lysed within phagolysosomes of these APCs. This releases both ATP and various peptides into the vacuole of the the APCs' phago-lysosome. It is hypnothesized that the ATP released from apoptotic cells into phagolysosomes of APCs opens $P2X_7$ receptors. This provides a pathway by which potentially immunogenic peptides from "foreign" apoptotic cells, and potentially "toleragenic" peptides from self apoptotic cells, enter the cytoplasm of APCs. These peptides then can be carried by TAP proteins into the endoplasmic reticulum where they associate with Class I MHC proteins. APCs and especially immature dendritic cells (1), recycle Class II MHC molecules from their phago-lysosomes to the plasma membrane. Thus peptide antigens released into phago-lysosomes are efficiently presented in association with Class II MHC proteins.

Antigen presenting cells (APCs) whose Class I and Class II MHC molecules contain antigen peptides elicit cytotoxic and helper T-lymphocytes. In some instances, these cytotoxic and helper lymphocytes cause tumor regression. Devised herein is a novel method for delivery of immunogenic peptides to macrophages and dendritic cells for presentation by Class I and Class II MHC proteins. The method uses as a delivery vehicle IgG-opsonized resealed red blood cell ghosts (rRBCg) containing immunogenic peptides for delivery to Class II MHC proteins, and IgG-opsonized-rRBCg containing immunogenic peptides and ATP for delivery to Class I MHC proteins. In the latter instance, the method makes use of $ATP^{4-}$-activated receptors (which may be $P2X_7$ or other ATP receptors) present in phagolysosomal vesicles to deliver immunogenic peptides to the cytoplasmic matrix of APCs (i.e., dendritic cells and macrophages).

Human red blood cell ghosts or other particles that can be filled with antigens (e.g., liposomes) and coated with ligands (IgG, oxidized lipids, sugars, polyanions), for receptors on antigen presenting cells (e.g., dendritic cells, Langerhans cells, monocytes, macrophages), are used as vehicles to encapsulate antigens (e.g., peptides, carbohydrates lipids, glycoproteins, glycolipids, lipoproteins), and adenosine triphosphate (ATP) or other ligands for ATP receptors (e.g. P2X7 and other ATP receptors)]. The antigens may be an antigen derived from, and/or induce immune responses that affect microbial pathogens, tumor cells, and/or immunoregulatory pathways. Ligands on the particle will promote ingestion of the particle by antigen presenting cells. Enzymes released into particle-containing phagosomes of antigen presenting cells will lyse the particle, releasing ATP and/or other substances that activate ATP receptors (such as P2X7 receptors, but not limited to these receptors) into these phagosomes. Activation of the receptors will create "pores" in the phagosomes' membranes through which antigens (e.g., antigenic peptides, carbohydrates, lipids) can enter the cytoplasm for processing and presentation to T-cells in association with conventional Class I MHC molecules, or other antigen presenting receptors.

The invention disclosed herein is useful as a vaccine, as a method for delivery of antigens to the cytoplasmic matrix of antigen presenting cells to induce immunity, to activate cytotoxic effects against tumor cells, and/or to suppress immunity/induce tolerance. The delivery system may also be used to deliver Th1 stimulatory cytokines (e.g., I1–I2, interfereon gamma) along with the antigen. The invention provided herein is a simple delivery system for purified antigens or crude cell extracts directly into the cytoplasmic matrix of antigen presenting cells for presentation by class I or II MHC and provides the advantage of not requiring isolation of host antigen presenting cells.

SUMMARY OF THE INVENTION

This invention provides a method of delivering an antigen to an Class I MHC receptor to induce immunity against the antigen in a subject having a disease which comprises: a) filling particles with the antigen and ATP resulting in an antigen- and ATP-filled particles (Ag/ATP-filled particles); b) coating the Ag/ATP-filled particles of step (a) with a ligand for an antigen presenting cell resulting in a ligand-coated Ag/ATP-filled particles; c) incubating the ligand-coated Ag/ATP-filled particles of step (b) with isolated ligand-binding antigen presenting cells (APCs) under conditions permitting the ligand-binding APCs to bind to the ligand-coated Ag/ATP-filled particles and APC phagolysosomes to ingest the ligand-coated Ag/ATP-filled particles to facilitate transfer of the ingested antigen from the phagolysosomes into cytoplasm such that the antigen is delivered to a Class I MHC receptor and is expressed on the surface of the APCs (Ag-APCs); and d) administering the antigen presenting cells (APCs) of step (c) to a subject having the disease so as induce Class I MHC presentation and elicit cytotoxic T-lymphocytes against the antigen, thereby inducing immunity against the antigen.

This invention provides a method of delivering an antigen to an Class I MHC receptor to induce immunity against the antigen in a subject having a disease which comprises: a) filling particles with the antigen and ATP resulting in an antigen- and ATP-filled particles (Ag/ATP-filled particles); b) coating the Ag/ATP-filled particles of step (a) with a ligand for an antigen presenting cell resulting in a ligand-coated Ag/ATP-filled particles; c) incubating the ligand-coated Ag/ATP-filled particles of step (b) with isolated ligand-binding antigen presenting cells (APCs) under conditions permitting the ligand-binding APCs to bind to the ligand-coated Ag/ATP-filled particles and APC phagolysosomes to ingest the ligand-coated Ag/ATP-filled particles to facilitate transfer of the ingested antigen from the phagolysosomes into cytoplasm such that the antigen is delivered to a Class I MHC receptor and is expressed on the surface of the APCs (Ag-APCs); d) incubating the Ag-APCs of step (c) with lymphocytes previously removed from the subject having the disease; and e) administering the incubated lymphocytes of step (d) to the subject so to induce immunity against the antigen in the subject.

This invention provides a method of delivering an antigen to an Class II MHC receptor to induce immunity against the antigen in a subject having a disease which comprises: a) filling particles with the antigen and ATP resulting in an antigen- and ATP-filled particles (Ag/ATP-filled particles); b) coating the Ag/ATP-filled particles of step (a) with a ligand for an antigen presenting cell resulting in a ligand-coated Ag/ATP-filled particles; c) incubating the ligand-coated Ag/ATP-filled particles of step (b) with isolated ligand-binding antigen presenting cells (APCs) under conditions permitting the ligand-binding APCs to bind to the ligand-coated Ag/ATP-filled particles and APC phagolysosomes to ingest the ligand-coated Ag/ATP-filled particles to facilitate transfer of the ingested antigen from the phagolysosomes into cytoplasm such that the antigen is delivered to a Class II MHC receptor and is expressed on the surface of the APCs (Ag-APCs); and d) administering the antigen presenting cells (APCs) of step (c) to a subject having the disease so as induce Class II MHC presentation and elicit helper T-lymphocytes against the antigen, thereby inducing immunity against the antigen.

This invention provides a method of delivering an antigen to an Class II MHC receptor to induce immunity against the antigen in a subject having a disease which comprises: a) filling particles with the antigen and ATP resulting in an antigen- and ATP-filled particles (Ag/ATP-filled particles); b) coating the Ag/ATP-filled particles of step (a) with a ligand for an antigen presenting cell resulting in a ligand-coated Ag/ATP-filled particles; c) incubating the ligand-coated Ag/ATP-filled particles of step (b) with isolated ligand-binding antigen presenting cells (APCs) under conditions permitting the ligand-binding APCs to bind to the ligand-coated Ag/ATP-filled particles and APC phagolysosomes to ingest the ligand-coated Ag/ATP-filled particles to facilitate transfer of the ingested antigen from the phagolysosomes into cytoplasm such that the antigen is delivered to a Class I MHC receptor and is expressed on the surface of the APCs (Ag-APCs); d) incubating the Ag-APCs of step (c) with lymphocytes previously removed from the subject having the disease; and e) administering the incubated lymphocytes of step (d) to the subject so as induce Class II MHC presentation and elicit helper T-lymphocytes so to induce immunity against the antigen in the subject.

This invention provides a method of delivering an antigen to an Class II MHC receptor to supress immunity against the antigen in a subject having a disease which comprises: a) filling particles with the antigen and ATP resulting in an antigen- and ATP-filled particles (Ag/ATP-filled particles); b) coating the Ag/ATP-filled particles of step (a) with a ligand for an antigen presenting cell resulting in a ligand-coated Ag/ATP-filled particles; c) incubating the ligand-coated Ag/ATP-filled particles of step (b) with isolated ligand-binding antigen presenting cells (APCs) under conditions permitting the ligand-binding APCs to bind to the ligand-coated Ag/ATP-filled particles and APC phagolysosomes to ingest the ligand-coated Ag/ATP-filled particles to facilitate transfer of the ingested antigen from the phagolysosomes into cytoplasm such that the antigen is delivered to a Class II MHC receptor and is expressed on the surface of the APCs (Ag-APCs); d) incubating the Ag-APCs of step (c) with lymphocytes previously removed from the subject having the disease; and e) administering the incubated lymphocytes of step (d) to the subject so as induce Class II MHC presentation and elicit suppressor T-lymphocytes so to supress immunity against the antigen in the subject.

This invention provides a method of delivering an antigen to an Class I MHC receptor to supress immunity against the antigen in a subject having a disease which comprises: a) filling particles with the antigen and ATP resulting in an antigen- and ATP-filled particles (Ag/ATP-filled particles); b) coating the Ag/ATP-filled particles of step (a) with a ligand for an antigen presenting cell resulting in a ligand-coated Ag/ATP-filled particles; c) incubating the ligand-coated Ag/ATP-filled particles of step (b) with isolated ligand-binding antigen presenting cells (APCs) under conditions permitting the ligand-binding APCs to bind to the ligand-coated Ag/ATP-filled particles and APC phagolysosomes to ingest the ligand-coated Ag/ATP-filled particles to facilitate transfer of the ingested antigen from the phagolysosomes into cytoplasm such that the antigen is delivered to a Class I MHC receptor and is expressed on the surface of the APCs (Ag-APCs); d) incubating the Ag-APCs of step (c) with lymphocytes previously removed from the subject having the disease; and e) administering the incubated lymphocytes of step (d) to the subject so as induce Class I MHC presentation and elicit suppressor T-lymphocytes so to supress immunity against the antigen in the subject.

This invention provides a method of delivering an antigen to an Class I MHC receptor to supress immunity against the antigen in a subject having a disease which comprises: a) filling particles with the antigen and ATP resulting in an antigen- and ATP-filled particles (Ag/ATP-filled particles); b) coating the Ag/ATP-filled particles of step (a) with a ligand for an antigen presenting cell resulting in a ligand-coated Ag/ATP-filled particles; c) incubating the ligand-coated Ag/ATP-filled particles of step (b) with isolated ligand-binding antigen presenting cells (APCs) under conditions permitting the ligand-binding APCs to bind to the ligand-coated Ag/ATP-filled particles and APC phagolysosomes to ingest the ligand-coated Ag/ATP-filled particles to facilitate transfer of the ingested antigen from the phagolysosomes into cytoplasm such that the antigen is delivered to a Class I MHC receptor and is expressed on the surface of the APCs (Ag-APCs); and d) administering the antigen presenting cells (APCs) of step (c) to a subject having the disease so as induce Class I MHC presentation and elicit suppressor T-lymphocytes so to supress immunity against the antigen in the subject.

This invention provides a method of delivering an antigen to an Class II MHC receptor to supress immunity against the antigen in a subject having a disease which comprises: a) filling particles with the antigen and ATP resulting in an antigen- and ATP-filled particles (Ag/ATP-filled particles); b) coating the Ag/ATP-filled particles of step (a) with a ligand for an antigen presenting cell resulting in a ligand-coated Ag/ATP-filled particles; c) incubating the ligand-coated Ag/ATP-filled particles of step (b) with isolated ligand-binding antigen presenting cells (APCs) under conditions permitting the ligand-binding APCs to bind to the ligand-coated Ag/ATP-filled particles and APC phagolysosomes to ingest the ligand-coated Ag/ATP-filled particles to facilitate transfer of the ingested antigen from the phagolysosomes into cytoplasm such that the antigen is delivered to a Class II MHC receptor and is expressed on the surface of the APCs (Ag-APCs); and d) administering the antigen presenting cells (APCs) of step (c) to a subject having the disease so as induce Class II MHC presentation and elicit suppressor T-lymphocytes so to supress immunity against the antigen in the subject.

BRIEF DESCRIPTION OF THE FIGURES

FIG. 1: Mouse Fetal Microglial Cells. Mouse fetal microglial cells were incubated with IgG opsonized red blood cell resealed ghosts (containing ATP and lucifer yellow). At the indicated times, the cells were observed under fluorescence microscopy. At 60 mins and 4 hours, the microglial cells ingested the particles and the dye is still contained within red blood cell ghosts. However, within 24 hrs, the dye has left the phagolysosome and now appears throughout the cytoplasm of the cells. (LY=lucifer yellow)

FIGS. 4A–4B: Determination of permeabilization of molecules from phago-lysosomes to the cytoplasmic matrix. IgG-coated resealed sheep red blood cell ghosts (IgG-rRBCg) containing the fluorescent dye Lucifer Yellow (LY) with or without ATP were prepared and these ghosts were incubated with monolayers of J774 macrophage-like cells at 37°. In IgG-rRBCg lacking ATP, apyrase was loaded into the RBCg to hydrolyze endogenous ATP. After 60 mins., monolayers were briefly exposed to distilled water to lyse undigested IgG-rRBCg+LY+ATP or IgG-rRBCg+LY and examined by phase and fluorescence microscopy. FIG. 4A. About 50% of the J774 cells that had ingested IgG-rRBCg+LY+ATP contained LY in their cytoplasmic and nuclear matrices. FIG. 4B. No LY was detected in the cytoplasmic or nuclear matrices of J774 cells that had ingested IgG-rRBCg+LY at any time from 0.5 to 48 hrs.

DETAILED DESCRIPTION OF THE INVENTION

This invention provides a method of delivering an antigen to an Class I MHC receptor to induce immunity against the antigen in a subject having a disease which comprises: a) filling particles with the antigen and ATP resulting in an antigen- and ATP-filled particles (Ag/ATP-filled particles); b) coating the Ag/ATP-filled particles of step (a) with a ligand for an antigen presenting cell resulting in a ligand-coated Ag/ATP-filled particles; c) incubating the ligand-coated Ag/ATP-filled particles of step (b) with isolated ligand-binding antigen presenting cells (APCs) under conditions permitting the ligand-binding APCs to bind to the ligand-coated Ag/ATP-filled particles and APC phagolysosomes to ingest the ligand-coated Ag/ATP-filled particles to facilitate transfer of the ingested antigen from the phagolysosomes into cytoplasm such that the antigen is delivered to a Class I MHC receptor and is expressed on the surface of the APCs (Ag-APCs); and d) administering the antigen presenting cells (APCs) of step (c) to a subject having the disease so as induce Class I MHC presentation and elicit cytotoxic T-lymphocytes against the antigen, thereby inducing immunity against the antigen.

In an embodiment of the above-described method of delivering an antigen to an Class I MHC receptor to induce immunity against the antigen in a subject having a disease, the particle is a type O red blood cell ghost. In another embodiment of the method the particle is a liposome. In an embodiment the ligand is selected from the group consisting of an immunoglobulin (IgG), complement component C3b, complement component C3bi, maleic anhydride, an oxidized lipid, a sugar, and a polyanion. In a further embodiment the antigen presenting cell is selected from the group consisting of a dendritic cell, a Langerhans cell, a monocyte, a mononuclear phagocyte, a macrophage, a Kupfer cell, a microglial cell, an osteoclast, and a bone marrow-derived leukocyte. In an embodiment the antigen is a purified antigen. In preferred embodiments the antigen is a cancer cell antigen, a bacterial antigen or a viral antigen. In an embodiment the antigen is a crude cell extract. In additional preferred embodiments the antigen is a cancer cell antigen, a bacterial antigen or a viral antigen. In an embodiment the antigen is selected from the group consisting of a peptide, a carbohydrate, a lipid, a glycoprotein, a glycolipid and a lipoprotein. In another embodiment of the above-described methods, the method further comprises delivering at least one stimulatory cytokine with the antigen to the cytoplasmic matrix of an antigen presenting cell which comprises in step (a) filling the particle with the stimulatory cytokine. In an embodiment the cytokine is IL-12, G-CSF, IL-4, GM-CSF or interferon gamma. In preferred embodiments the immunity induced is against a bacterial or viral antigen. In still further preferred embodiments the immunity induced is against a cancerous tumor. In preferred embodiments the disease is a bacterial infection or a viral infection. In additional preferred embodiments the disease is cancer.

This invention provides a method of delivering an antigen to an Class I MHC receptor to induce immunity against the antigen in a subject having a disease which comprises: a) filling particles with the antigen and ATP resulting in an antigen- and ATP-filled particles (Ag/ATP-filled particles); b) coating the Ag/ATP-filled particles of step (a) with a ligand for an antigen presenting cell resulting in a ligand-coated Ag/ATP-filled particles; c) incubating the ligand-coated Ag/ATP-filled particles of step (b) with isolated ligand-binding antigen presenting cells (APCs) under conditions permitting the ligand-binding APCs to bind to the ligand-coated Ag/ATP-filled particles and APC phagolysosomes to ingest the ligand-coated Ag/ATP-filled particles to facilitate transfer of the ingested antigen from the phagolysosomes into cytoplasm such that the antigen is delivered to a Class I MHC receptor and is expressed on the surface of the APCs (Ag-APCs); d) incubating the Ag-APCs of step (c) with lymphocytes previously removed from the subject having the disease; and e) administering the incubated lymphocytes of step (d) to the subject so to induce immunity against the antigen in the subject.

In an embodiment of the above-described method of delivering an antigen to an Class I MHC receptor to induce immunity against the antigen in a subject having a disease, the particle is a type O red blood cell ghost. In an embodiment the particle is a liposome. In another embodiment the ligand is selected from the group consisting of an immunoglobulin (IgG), complement component C3b, complement component C3bi, maleic anhydride, an oxidized lipid, a sugar, and a polyanion. In a further embodiment the antigen presenting cell is selected from the group consisting of a dendritic cell, a Langerhans cell, a monocyte, a mononuclear phagocyte, a macrophage, a Kupfer cell, a microglial cell, an osteoclast, and a bone marrow-derived leukocyte. In an embodiment the antigen is a purified antigen. In a preferred embodiment the purified antigen is a cancer cell antigen, a bacterial antigen or a viral antigen. In an embodiment the antigen is a crude cell extract. In another preferred embodiment the crude cell extract antigen is a cancer cell antigen, a bacterial antigen or a viral antigen. In an embodiment the antigen is selected from the group consisting of a peptide, a carbohydrate, a lipid, a glycoprotein, a glycolipid and a lipoprotein. In another embodiment of the above-described method the method further comprises delivering at least one stimulatory cytokine with the antigen to the cytoplasmic matrix of an antigen presenting cell which comprises in step (a) filling the particle with the stimulatory cytokine. In an embodiment the cytokine is IL-12, G-CSF, IL-4, GM-CSF or interferon gamma. In a preferred embodiment the immunity induced is against a bacterial or viral antigen. In another preferred embodiment the immunity induced is against a cancerous tumor. In a further preferred embodiment the disease is a bacterial infection or a viral infection. In a still further preferred embodiment the disease is cancer.

This invention provides a method of delivering an antigen to an Class II MHC receptor to induce immunity against the antigen in a subject having a disease which comprises: a) filling particles with the antigen and ATP resulting in an antigen- and ATP-filled particles (Ag/ATP-filled particles); b) coating the Ag/ATP-filled particles of step (a) with a ligand for an antigen presenting cell resulting in a ligand-coated Ag/ATP-filled particles; c) incubating the ligand-coated Ag/ATP-filled particles of step (b) with isolated ligand-binding antigen presenting cells (APCs) under conditions permitting the ligand-binding APCs to bind to the ligand-coated Ag/ATP-filled particles and APC phagolysosomes to ingest the ligand-coated Ag/ATP-filled particles to facilitate transfer of the ingested antigen from the phagolysosomes into cytoplasm such that the antigen is delivered to a Class II MHC receptor and is expressed on the surface of the APCs (Ag-APCs); and d) administering the antigen presenting cells (APCs) of step (c) to a subject having the disease so as induce Class II MHC presentation and elicit helper T-lymphocytes against the antigen, thereby inducing immunity against the antigen.

In an embodiment of the above-described method of delivering an antigen to an Class II MHC receptor to induce immunity against the antigen in a subject having a disease the particle is a type O red blood cell ghost. In an embodiment the particle is a liposome. In another embodiment the ligand is selected from the group consisting of an immunoglobulin (IgG), complement component C3b, complement component C3bi, maleic anhydride, an oxidized lipid, a sugar, and a polyanion. In a further embodiment the antigen presenting cell is selected from the group consisting of a dendritic cell, a Langerhans cell, a monocyte, a mononuclear phagocyte, a macrophage, a Kupfer cell, a microglial cell, an osteoclast, and a bone marrow-derived leukocyte. In an embodiment the antigen is a purified antigen. In a preferred embodiment the purified antigen is a cancer cell antigen, a bacterial antigen or a viral antigen. In an embodiment the antigen is a crude cell extract. In an embodiment the crude cell extract antigen is a cancer cell antigen, a bacterial antigen or a viral antigen. In an embodiment the antigen is selected from the group consisting of a peptide, a carbohydrate, a lipid, a glycoprotein, a glycolipid and a lipoprotein. In an embodiment of the above-described methods, the method further comprising delivering at least one stimulatory cytokine with the antigen to the cytoplasmic matrix of an antigen presenting cell which comprises in step (a) filling the particle with the stimulatory cytokine. In an embodiment the cytokine is IL-12, G-CSF, IL-4, GM-CSF or interferon gamma. In a preferred eembodiment the immunity induced is against a bacterial or viral antigen. In another preferred eembodiment the immunity induced is against a cancerous tumor. In other preferred embodiments the disease is a bacterial infection or a viral infection. In further preferred eembodiment the disease is cancer.

This invention provides a method of delivering an antigen to an Class II MHC receptor to induce immunity against the antigen in a subject having a disease which comprises: a) filling particles with the antigen and ATP resulting in an antigen- and ATP-filled particles (Ag/ATP-filled particles); b) coating the Ag/ATP-filled particles of step (a) with a ligand for an antigen presenting cell resulting in a ligand-coated Ag/ATP-filled particles; c) incubating the ligand-coated Ag/ATP-filled particles of step (b) with isolated ligand-binding antigen presenting cells (APCs) under conditions permitting the ligand-binding APCs to bind to the ligand-coated Ag/ATP-filled particles and APC phagolysosomes to ingest the ligand-coated Ag/ATP-filled particles to facilitate transfer of the ingested antigen from the phagolysosomes into cytoplasm such that the antigen is delivered to a Class I MHC receptor and is expressed on the surface of the APCs (Ag-APCs); d) incubating the Ag-APCs of step (c) with lymphocytes previously removed from the subject having the disease; and e) administering the incubated lymphocytes of step (d) to the subject so as induce Class II MHC presentation and elicit helper T-lymphocytes so to induce immunity against the antigen in the subject.

In an embodiment of the above-described method of delivering an antigen to an Class II MHC receptor to induce immunity against the antigen in a subject having a disease the particle is a type O red blood cell ghost. In an embodiment the particle is a liposome. In another embodiment the ligand is selected from the group consisting of an immunoglobulin (IgG), complement component C3b, complement component C3bi, maleic anhydride, an oxidized lipid, a sugar, and a polyanion. In a further embodiment the antigen presenting cell is selected from the group consisting of a dendritic cell, a Langerhans cell, a monocyte, a mononuclear phagocyte, a macrophage, a Kupfer cell, a microglial cell, an osteoclast, and a bone marrow-derived leukocyte. In an embodiment the antigen is a purified antigen. In a preferred embodiment the purified antigen is a cancer cell antigen, a bacterial antigen or a viral antigen. In another embodiment the antigen is a crude cell extract. In a preferred embodiment the crude cell extract antigen is antigen is a cancer cell antigen, a bacterial antigen or a viral antigen. In an embodiment the antigen is selected from the group consisting of a peptide, a carbohydrate, a lipid, a glycoprotein, a glycolipid and a lipoprotein. In another embodiment of the above-described methods, the method further comprises delivering at least one stimulatory cytokine with the antigen to the cytoplasmic matrix of an antigen presenting cell which comprises in step (a) filling the particle with the stimulatory cytokine. In an embodiment the cytokine is IL-12, G-CSF, IL-4, GM-CSF or interferon gamma. In a preferred embodiment the immunity induced is against a bacterial or viral antigen. In another preferred embodiment the immunity induced is against a cancerous tumor. In further preferred embodiment the disease is a bacterial infection or a viral infection. In another preferred embodiment the disease is cancer.

This invention provides a method of delivering an antigen to an Class II MHC receptor to supress immunity against the antigen in a subject having a disease which comprises: a) filling particles with the antigen and ATP resulting in an antigen- and ATP-filled particles (Ag/ATP-filled particles); b) coating the Ag/ATP-filled particles of step (a) with a ligand for an antigen presenting cell resulting in a ligand-coated Ag/ATP-filled particles; c) incubating the ligand-coated Ag/ATP-filled particles of step (b) with isolated ligand-binding antigen presenting cells (APCs) under conditions permitting the ligand-binding APCs to bind to the ligand-coated Ag/ATP-filled particles and APC phagolysosomes to ingest the ligand-coated Ag/ATP-filled particles to facilitate transfer of the ingested antigen from the phagolysosomes into cytoplasm such that the antigen is delivered to a Class II MHC receptor and is expressed on the surface of the APCs (Ag-APCs); d) incubating the Ag-APCs of step (c) with lymphocytes previously removed from the subject having the disease; and e) administering the incubated lymphocytes of step (d) to the subject so as induce Class II MHC presentation and elicit suppressor T-lymphocytes so to supress immunity against the antigen in the subject.

In an embodiment of the above-described method of delivering an antigen to an Class II MHC receptor to supress immunity against the antigen in a subject having a disease the particle is a type O red blood cell ghost. In an embodiment the particle is a liposome. In another embodiment the ligand is selected from the group consisting of an immunoglobulin (IgG), complement component C3b, complement component C3bi, maleic anhydride, an oxidized lipid, a sugar, and a polyanion. In a further embodiment the antigen presenting cell is selected from the group consisting of a dendritic cell, a Langerhans cell, a monocyte, a mononuclear phagocyte, a macrophage, a Kupfer cell, a microglial cell, an osteoclast, and a bone marrow-derived leukocyte. In an embodiment the antigen is a purified antigen. In a preferred embodiment of the purified antigen, the antigen is an antigen of a transplant organ. In an embodiment the transplant organ antigen is allogeneic antigen, a syngeneic antigen, or a xenogenic antigen. In another embodiment the antigen is a crude cell extract. In a preferred embodiment of the crude cell extract antigen the antigen is an antigen of a transplant organ. In an embodiment the transplant organ antigen is allogeneic antigen, a syngeneic antigen, or a xenogenic antigen. In another embodiment the antigen is selected from the group consisting of a peptide, a carbohydrate, a lipid, a glycoprotein, a glycolipid and a lipoprotein. In another embodiment of the above-described methods, the method further comprises delivering at least one stimulatory cytokine with the antigen to the cytoplasmic matrix of an antigen presenting cell which comprises in step (a) filling the particle with the stimulatory cytokine. In an embodiment the cytokine is IL-12, G-CSF, IL-4, GM-CSF or interferon gamma. In a preferred embodiment the immunity suppressed is immunity against a transplanted organ or tissue. In another preferred embodiment the immunity suppressed is immunity against organs of the subject. In still another preferred embodiment the disease is an autoimmune disease or rejection of a transplanted organ or tissue.

This invention provides a method of delivering an antigen to an Class I MHC receptor to supress immunity against the antigen in a subject having a disease which comprises: a) filling particles with the antigen and ATP resulting in an antigen- and ATP-filled particles (Ag/ATP-filled particles); b) coating the Ag/ATP-filled particles of step (a) with a ligand for an antigen presenting cell resulting in a ligand-coated Ag/ATP-filled particles; c) incubating the ligand-coated Ag/ATP-filled particles of step (b) with isolated ligand-binding antigen presenting cells (APCs) under conditions permitting the ligand-binding APCs to bind to the ligand-coated Ag/ATP-filled particles and APC phagolysosomes to ingest the ligand-coated Ag/ATP-filled particles to facilitate transfer of the ingested antigen from the phagolysosomes into cytoplasm such that the antigen is delivered to a Class I MHC receptor and is expressed on the surface of the APCs (Ag-APCs); d) incubating the Ag-APCs of step (c) with lymphocytes previously removed from the subject having the disease; and e) administering the incubated lymphocytes of step (d) to the subject so as induce Class I MHC presentation and elicit suppressor T-lymphocytes so to supress immunity against the antigen in the subject.

In an embodiment of the above-described method of delivering an antigen to an Class I MHC receptor to supress immunity against the antigen in a subject having a disease the particle is a type O red blood cell ghost. In another embodiment the particle is a liposome. In a further embodiment the ligand is selected from the group consisting of an immunoglobulin (IgG), complement component C3b, complement component C3bi, maleic anhydride, an oxidized lipid, a sugar, and a polyanion. In another embodiment the antigen presenting cell is selected from the group consisting of a dendritic cell, a Langerhans cell, a monocyte, a mononuclear phagocyte, a macrophage, a Kupfer cell, a microglial cell, an osteoclast, and a bone marrow-derived leukocyte. In an embodiment the antigen is a purified antigen. In a preferred embodiment of the purified antigen, the antigen is an antigen of a transplant organ. In an embodiment the transplant organ antigen is allogeneic antigen, a syngeneic antigen, or a xenogenic antigen. In another embodiment the antigen is a purified antigen the antigen is a crude cell extract. In a preferred embodiment of the crude cell extract antigen, the antigen is an antigen of a transplant organ. In an embodiment the transplant organ antigen is allogeneic antigen, a syngeneic antigen, or a xenogenic antigen. In another embodiment the antigen is selected from the group consisting of a peptide, a carbohydrate, a lipid, a glycoprotein, a glycolipid and a lipoprotein. In an embodiment of the above-described methods, the method further comprises delivering at least one stimulatory cytokine with the antigen to the cytoplasmic matrix of an antigen presenting cell which comprises in step (a) filling the particle with the stimulatory cytokine. In an embodiment the cytokine is IL-12, G-CSF, IL-4, GM-CSF or interferon gamma. In a preferred embodiment the immunity suppressed is immunity against a transplanted organ or tissue. In other preferred embodiments the immunity suppressed is immunity against organs of the subject. In additional preferred embodiments the disease is an autoimmune disease or rejection of a transplanted organ or tissue.

This invention provides a method of delivering an antigen to an Class I MHC receptor to supress immunity against the antigen in a subject having a disease which comprises: a) filling particles with the antigen and ATP resulting in an antigen- and ATP-filled particles (Ag/ATP-filled particles); b) coating the Ag/ATP-filled particles of step (a) with a ligand for an antigen presenting cell resulting in a ligand-coated Ag/ATP-filled particles; c) incubating the ligand-coated Ag/ATP-filled particles of step (b) with isolated ligand-binding antigen presenting cells (APCs) under conditions permitting the ligand-binding APCs to bind to the ligand-coated Ag/ATP-filled particles and APC phagolysosomes to ingest the ligand-coated Ag/ATP-filled particles to facilitate transfer of the ingested antigen from the phagolysosomes into cytoplasm such that the antigen is delivered to a Class I MHC receptor and is expressed on the surface of the APCs (Ag-APCs); and d) administering the antigen presenting cells (APCs) of step (c) to a subject having the disease so as induce Class I MHC presentation and elicit suppressor T-lymphocytes so to supress immunity against the antigen in the subject.

In an embodiment of the above-described method of delivering an antigen to an Class I MHC receptor to supress immunity against the antigen in a subject having a disease the particle is a type O red blood cell ghost. In another embodiment the particle is a liposome. In a further embodiment the ligand is selected from the group consisting of an immunoglobulin (IgG), complement component C3b, complement component C3bi, maleic anhydride, an oxidized lipid, a sugar, and a polyanion. In yet another embodiment the antigen presenting cell is selected from the group consisting of a dendritic cell, a Langerhans cell, a monocyte, a mononuclear phagocyte, a macrophage, a Kupfer cell, a microglial cell, an osteoclast, and a bone marrow-derived leukocyte. In an embodiment the antigen is a purified antigen. In a preferred embodiment of the purified antigen the antigen is an antigen of a transplant organ. In an embodiment the transplant organ antigen is allogeneic antigen, a syngeneic antigen, or a xenogenic antigen. In another embodiment the antigen is a crude cell extract. In a preferred embodiment of the a crude cell extract the antigen is an antigen of a transplant organ. In an embodiment the transplant organ antigen is allogeneic antigen, a syngeneic antigen, or a xenogenic antigen. In another embodiment the antigen is selected from the group consisting of a peptide, a carbohydrate, a lipid, a glycoprotein, a glycolipid and a lipoprotein. In an embodiment of the above-described methods, the method further comprises delivering at least one stimulatory cytokine with the antigen to the cytoplasmic matrix of an antigen presenting cell which comprises in step (a) filling the particle with the stimulatory cytokine. In an embodiment the cytokine is IL-12, G-CSF, IL-4, GM-CSF or interferon gamma. In a preferred embodiment the immunity suppressed is immunity against a transplanted organ or tissue. In another preferred embodiment the immunity suppressed is immunity against organs of the subject. In a still further preferred embodiment the disease is an autoimmune disease or rejection of a transplanted organ or tissue.

This invention provides a method of delivering an antigen to an Class II MHC receptor to supress immunity against the antigen in a subject having a disease which comprises: a) filling particles with the antigen and ATP resulting in an antigen- and ATP-filled particles (Ag/ATP-filled particles); b) coating the Ag/ATP-filled particles of step (a) with a ligand for an antigen presenting cell resulting in a ligand-coated Ag/ATP-filled particles; c) incubating the ligand-coated Ag/ATP-filled particles of step (b) with isolated ligand-binding antigen presenting cells (APCs) under conditions permitting the ligand-binding APCs to bind to the ligand-coated Ag/ATP-filled particles and APC phagolysosomes to ingest the ligand-coated Ag/ATP-filled particles to facilitate transfer of the ingested antigen from the phagolysosomes into cytoplasm such that the antigen is delivered to a Class II MHC receptor and is expressed on the surface of the APCs (Ag-APCs); and d) administering the antigen presenting cells (APCs) of step (c) to a subject having the disease so as induce Class II MHC presentation and elicit suppressor T-lymphocytes so to supress immunity against the antigen in the subject.

In the above-described method of delivering an antigen to an Class II MHC receptor to supress immunity against the antigen in a subject having a disease the particle is a type O red blood cell ghost. In another embodiment of the method method the particle is a liposome. In a further embodiment the ligand is selected from the group consisting of an immunoglobulin (IgG), complement component C3b, complement component C3bi, maleic anhydride, an oxidized lipid, a sugar, and a polyanion. In another embodiment the antigen presenting cell is selected from the group consisting of a dendritic cell, a Langerhans cell, a monocyte, a mononuclear phagocyte, a macrophage, a Kupfer cell, a microglial cell, an osteoclast, and a bone marrow-derived leukocyte. In yet another embodiment the antigen is a purified antigen. In a preferred embodiment of the purified antigen, the antigen is an antigen of a transplant organ. In an embodiment the transplant organ antigen is allogeneic antigen, a syngeneic antigen, or a xenogenic antigen. In another embodiment the antigen is a crude cell extract. In a preferred embodiment of the crude cell extract antigen, the antigen is an antigen of a transplant organ. In an embodiment the transplant organ antigen is allogeneic antigen, a syngeneic antigen, or a xenogenic antigen. In a further embodiment the antigen is selected from the group consisting of a peptide, a carbohydrate, a lipid, a glycoprotein, a glycolipid and a lipoprotein. In an embodiment of the above-described methods, the method further comprises delivering at least one stimulatory cytokine with the antigen to the cytoplasmic matrix of an antigen presenting cell, step (a) comprises filling the particle with the stimulatory cytokine. In additional embodiments the cytokine is IL-12, G-CSF, IL- 4, GM-CSF or interferon gamma. In a preferred embodiment the immunity suppressed is immunity against a transplanted organ or tissue. In another preferred embodiment the immunity suppressed is immunity against organs of the subject. In further preferred embodiments the disease is an autoimmune disease or rejection of a transplanted organ or tissue.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

First Series of Experiments

Methods and Materials

Preparation of Red Blood Cell ghosts loaded with either indicator dye, peptide (antigen) or protein.

Lyse either human or sheep red blood cells in hypotonic KCl buffer containing 5 mM ATP and either a) indicator dye such as lucifer yellow at 5 mg/ml, b) peptides such as fluorescence-labelled ovalbumin, c) proteins, or d) lysate of tumor cells at 4° C. for 20 mins. The same procedure can be done without adding ATP to the red blood cells.

Reseal ghosts in hypertonic KCl buffer to achieve isotonicity at 37° C. for 40 mins.

Wash cells several times in phosphate buffered saline.

Opsonize (using published techniques) the red cells with the appropriate ligand which could be a) immunoglobulin (IgG), b) complement component C3b, c)complement component C3bi, d) maleic anhydride or others.

Add these opsonized ATP/peptide red blood cell resealed ghosts to isolated human dendritic cells obtained from either blood, bone marrow, brain, liver, skin or lymph nodes. Let the dendritic cells ingest the opsonized ATP/peptide red blood cell resealed ghosts for several (3–24) hours with the appropriate cytokine such as GCSF, IL4, GMCSF, gamma interferon. The peptide will then be transferred from the phagolysosomes to other cytoplasmic compartments and eventually will be expressed as MHC class I antigens on the surface of the dendritic cells.

Either a) co-incubate these dendritic cells with lymphocytes in vitro for 6 hrs and then reinject the lymphocytes into the patient or b) inject these dendritic cells directly into the patient.

These dendritic cells should then induce class I MHC presentation and elicit cytotoxic T cells against the desired antigen. For example this method may be effective in generating an immunological response against tumors or microbial agents.

Opsonization of the red blood cell ghosts with C3bi enhances the transfer of lucifer yellow to the ctyoplasm.

Shown herein is preparation of opsonized ATP/peptide red blood cell resealed ghosts containing either an indicator dye such as lucifer yellow (LY) or a peptide such as fluorescein-conjugated ovalbumin peptide (amino acids 257–264).

Figure 2:
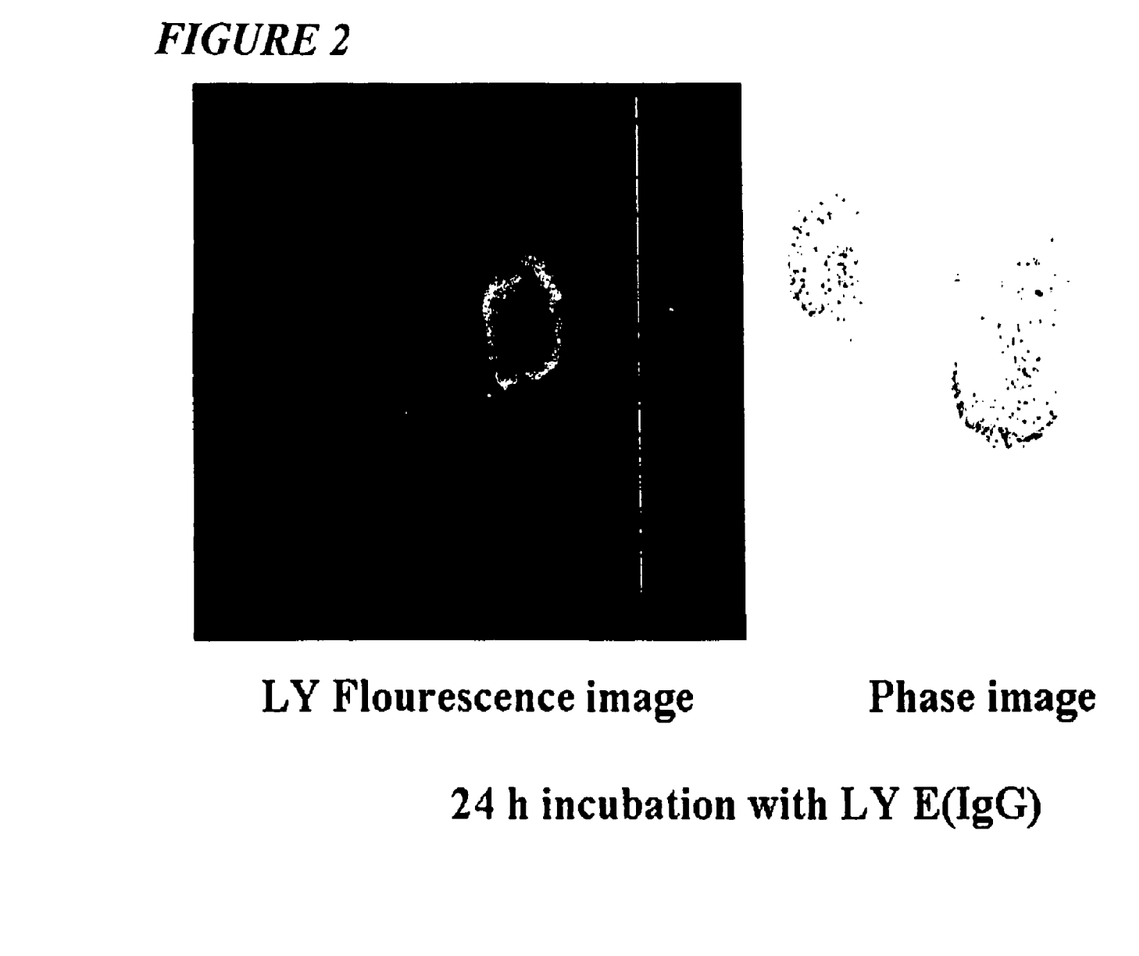
FIG. 2: Human Monocyte Derived Dendritic Cells. At 24 hours, the dendritic cells that have ingested the IgG opsonized red blood cell resealed ghosts (containing ATP and lucifer yellow) now express the dye throughout the cytoplasm of the cell.
Figure 3:
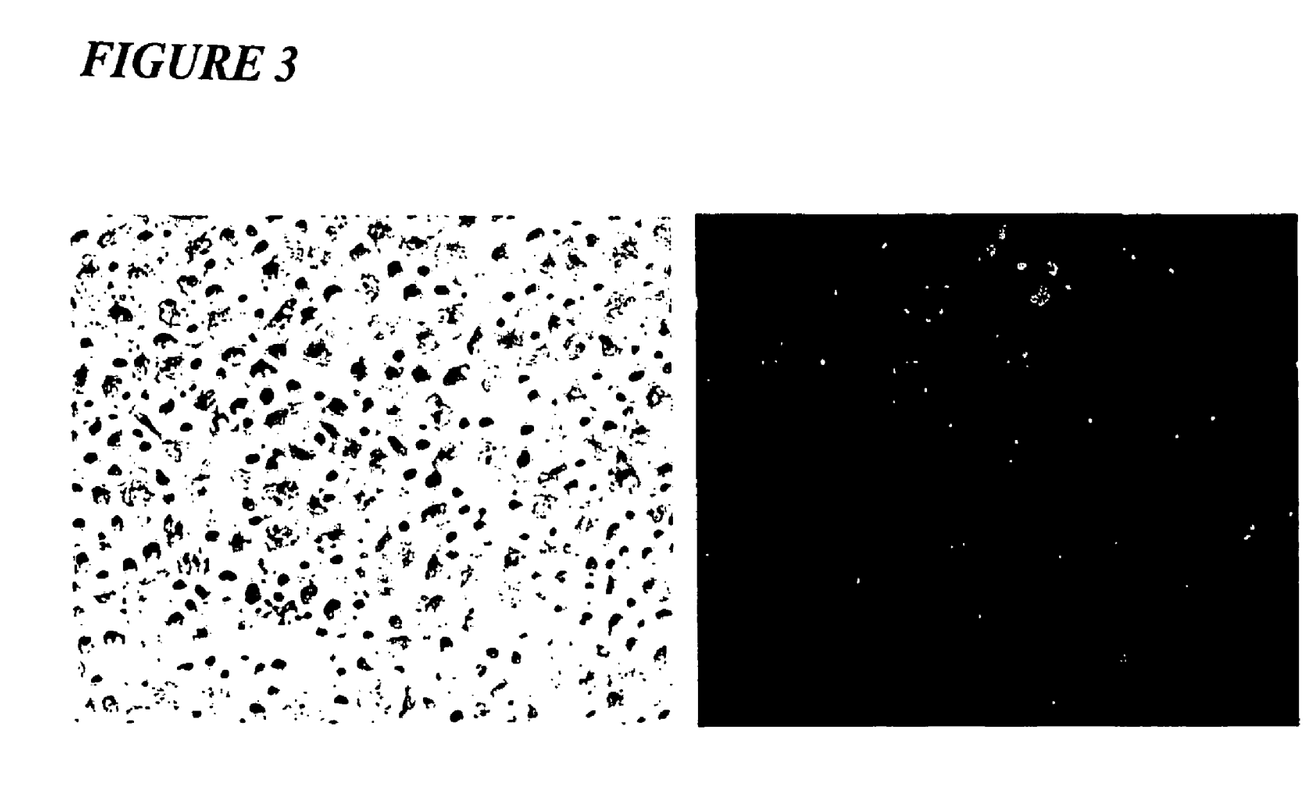
FIG. 3: B6 Bone Marrow Derived Dendritic Cells 3 hr Fl-Ova-E(IgG). Mouse Bone marrow derived dendritic cells were incubated for about 4 hours with IgG opsonized red blood cell resealed ghosts (containing ATP and fluorochrome conjugated ovalbumin peptide [fl-ova]). In many of the cells, the fluorochrome dye is observed to be localized throughout the cytoplasm rather than in phagolysosomes.

These opsonized ATP/peptide red blood cell resealed ghosts are now ingested by either mouse microglial cells (an antigen presenting macrophage like cell found in the brain) (FIG. 1), human blood monocyte derived dendritic cells (FIG. 2) or bone derived mouse dendritic cells (FIG. 3).

Figure 1:
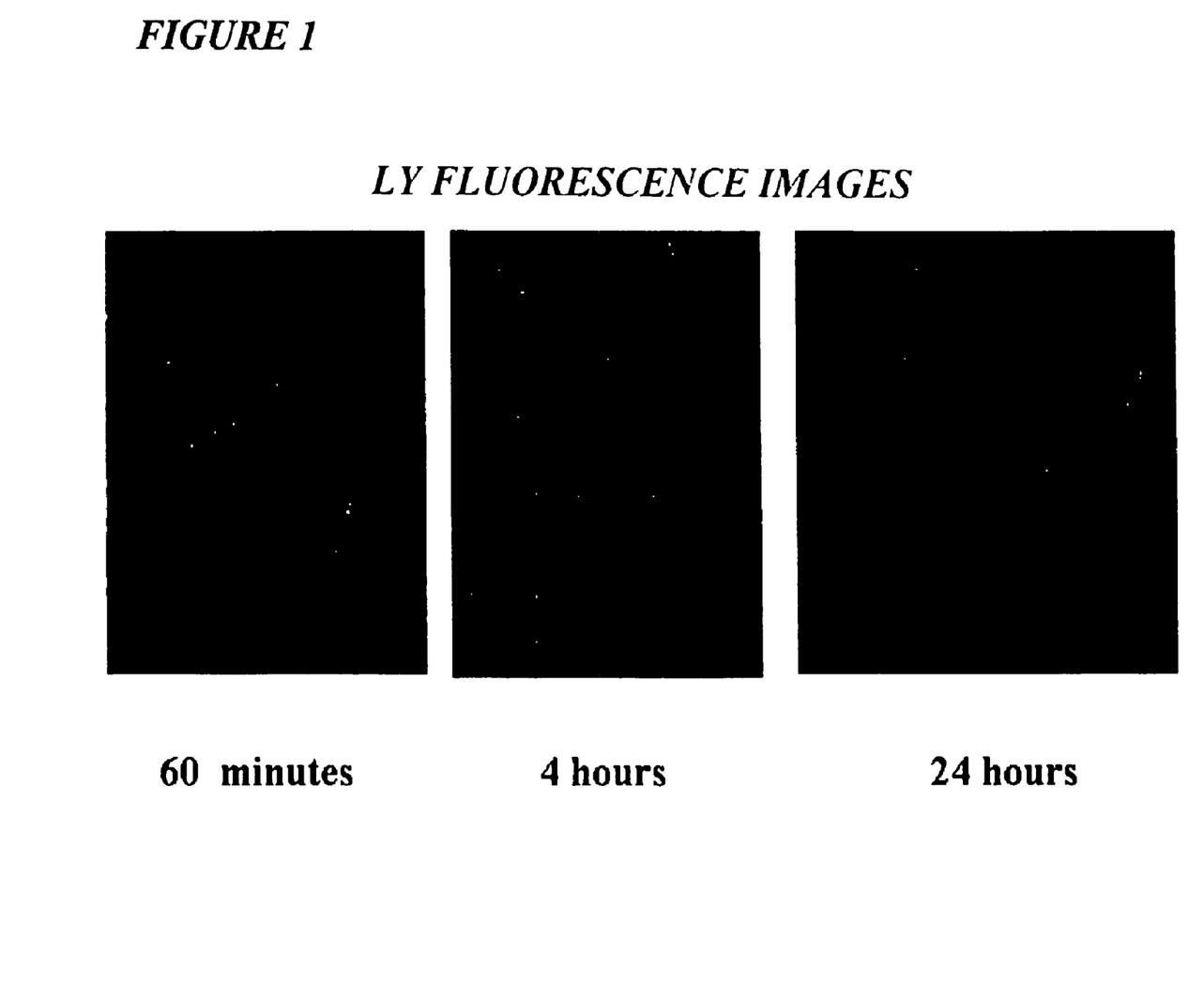

Within 24 hr, the indicator dye or indicator peptide is transferred from the phagolysosome to one or more different cytoplasmic compartments which allows the peptide to then be processed and presented to class I MHC.

It is shown herein that if a peptide such as ovalbumin is loaded into the IgG opsonized red blood cell resealed ghosts and then incubated with mouse bone derived dendritic cells—the dendritic cells will present class I MHC and induce cytotoxic CD8 lymphocytes as measured by the capacity of these lymphocytes to proliferate in response to co-incubation of the dendritic cells with CD8 lymphocytes. (Table 1)

Table 1: Mouse Bone marrow derived dendritic cells prepared as described in FIG. 3 were incubated with the appropriate isogenic spleen derived CD8 lymphocytes for several hours and then the CTL response was assayed by radiolabeled thymidine incorporation into the lymphocytes indicating a proliferative response mediated via class I MHC.

TABLE 1

Class I antigen presentation via Ova peptide

| Mouse bone derived dendritic cells treated with: | CTL Assay-<br>$^3$H-thymidine uptake<br>(proliferation assay-cpm)* |
|---|---|
| Soluble Ova protein (10 mg/ml) | 160,000 |
| Soluble Ova peptide (100 ng/ml) | 90,000 |
| E(IgG) loaded with ATP and Ova peptide (100 ng/ml) | 130,000 |
| E(IgG) loaded with ATP and Ova peptide (10 ng/ml) | 22,000 |
| E(IgG) loaded with apyrase and Ova peptide (10 ng/ml) | 23,000 |

*in the absence of added antigen or with RBC's: cpms were <500.

Second Series of Experiments

Figures 1B, 4B:
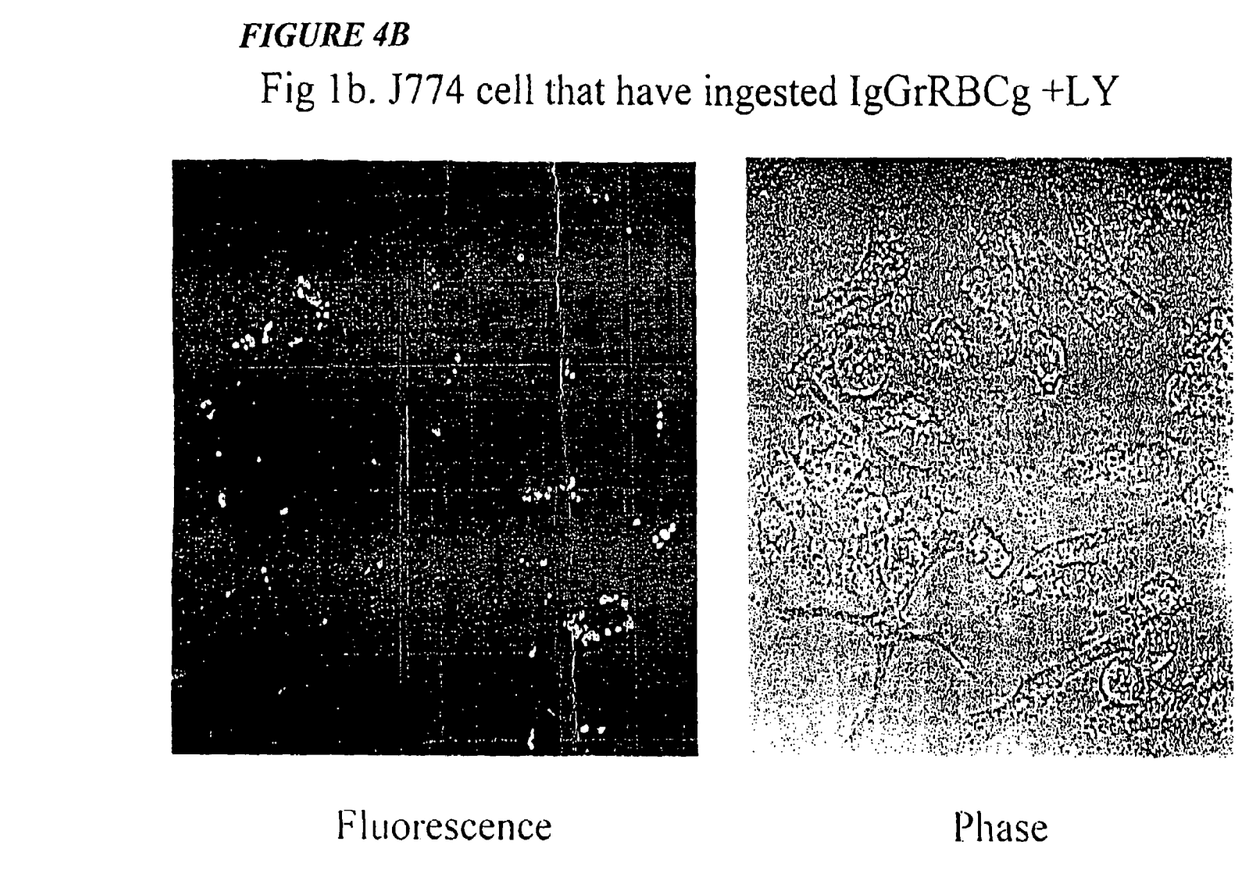
Figure 4A:
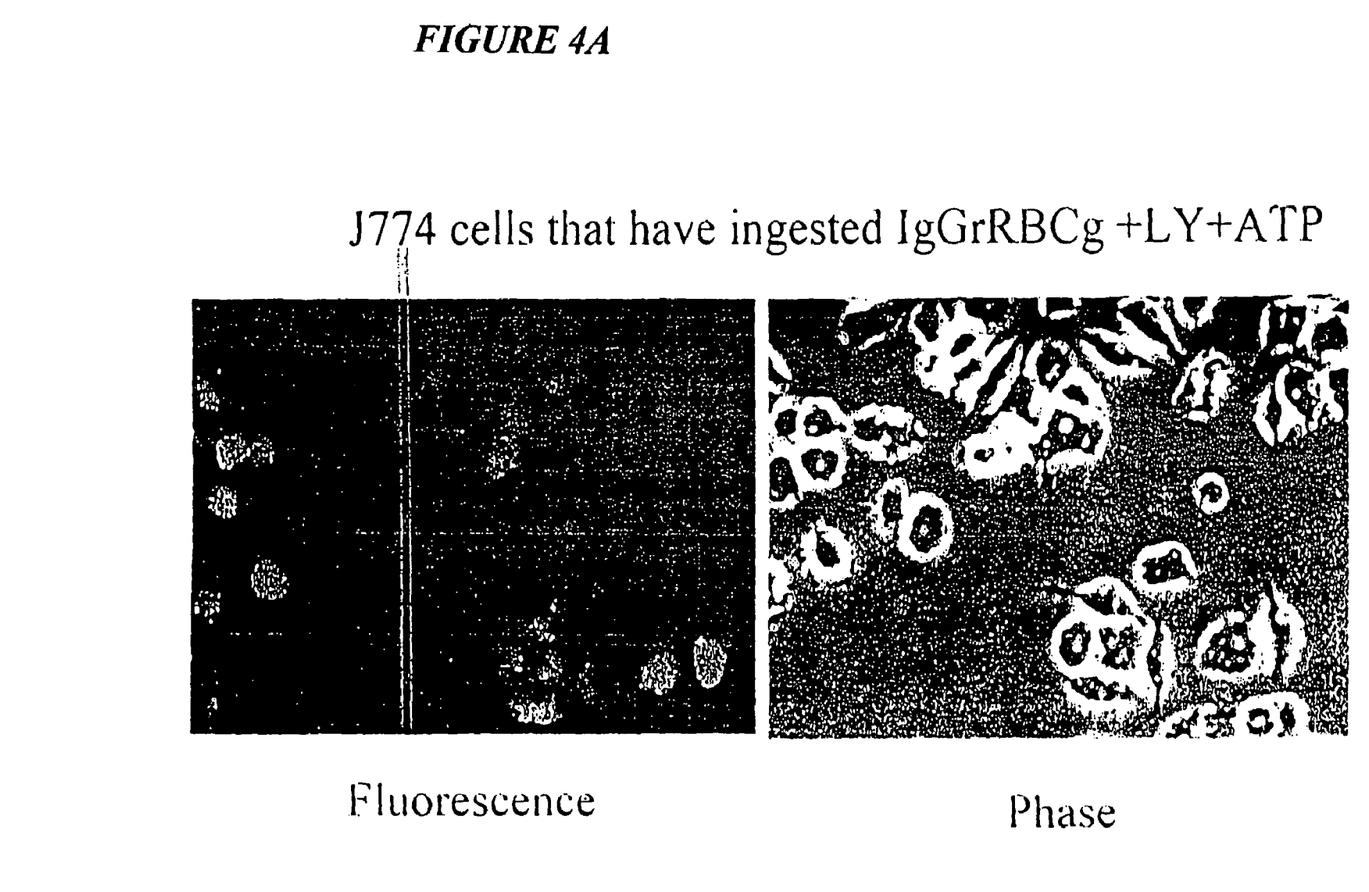

To determine whether $P2X_7$ receptors mediate permeabilization of molecules from phago-lysosomes to the cytoplasmic matrix, prepared were IgG-coated resealed sheep red blood cell ghosts (IgG-rRBCg) containing the fluorescent dye Lucifer Yellow (LY) with or without ATP, and these ghosts were incubated with monolayers of J774 macrophage-like cells at 37° C. In IgG-rRBCg lacking ATP, apyrase was loaded into the RBCg to hydrolyze endogenous ATP. After 60 minutes, monolayers were briefly exposed to distilled water to lyse uningested IgG-rRBCg+LY+ATP or IgG-rRBCg+LY and examined by phase and fluorescence microscopy. As expected, >90% of the macrophages ingested one or more IgG-rRBCg+LY+ATP or IgG-rRBCg+LY. These brightly fluorescent IgG-rRBCgs were contained in phago-lysosomes in the J774 cells' cytoplasm. About 50% of the J774 cells that had ingested IgG-rRBCg+LY+ATP contained LY in their cytoplasmic and nuclear matrices (see FIG. 4A). The LY remained in the cytoplasmic and nuclear matrices of J774 cells that ingested IgGrRBCg+LY+ATP for 48 hours, the longest time point examined. In contrast, no LY was detected in the cytoplasmic or nuclear matrices of J774 cells that had ingested IgGrRBCg+LY at any time from 0.5 to 48 hours (FIG. 4B). Similar results were obtained using thioglycollate elicited mouse peritoneal macrophages (data not shown). To confirm these results J774 cells which lack $P2X_7$ receptors (J774-$P2X_7$ null) were used. These cells were selected and characterized as described (7). About 60% of J774-$P2X_7$ null cells ingested IgGrRBCg+LY+ATP but none of these cells exhibited LY in their cytoplasmic or nuclear matrices 0.5 to 48 hours later. All the LY remained within the phago-lysosomes (data not shown).

Previous studies confirmed that dyes such as fura 2, ~850 M.W. (8), and LY covalently linked to the alpha amino group of glycyl-glycine (M.W. ~632) (Silverstein, unpublished observations), penetrate plasma membrane pores formed by $ATP^{4-}$-activated $P2X_7$ receptors of J774 cells. Thus, ATP-activated $P2X_7$ receptors are permeable to peptides. Since T-cell receptors recognize foreign peptides 9 to 10 amino acids in length in association with Class I MHC molecules and the average M.W. for a nona-peptide is ~900, there is every reason to believe that pores formed by $P2X_7$ receptors will be permeable to nona- and deca-peptides.

Experimental plan: 1. Whether murine macrophages and J774 cells present the β-galactosidase nona-peptide TPH- PARIGL (SEQ ID. NO:1) in a Class I MHC restricted fashion when they ingest IgGrRBCg+ATP.

Peritoneal macrophages from Balb/c mice, or J774 cells ($H-2L^d$), loaded with TPHPARIGL (SEQ ID. NO:1) (residues 876–884 of E. coli β-galactosidase) are lysed by the $H-2L^d$-restricted murine cytotoxic T-cell line 0805B (CTL0805B). CTL0805B cells, kindly provided by Dr. Michael Bevan, University of Washington. IgG-rRBCg will be loaded with TPHPARIGL plus LY, or TPHPARIGL plus LY plus 5 mM ATP (e.g., IgGrRBCg+TPHPARIGL (SEQ ID. NO:1)+LY+ATP or IgGrRBCg+TPHPARIGL(SEQ ID. NO:1)+LY), washed to remove free peptide, and incubated at 37° C. for 1 hour with monolayers of macrophages or of J774 cells. (Ghosts containing TPHPARIGL (SEQ ID. NO:1), LY and ATP will be used in the initial experiments to confirm that these ghosts are being ingested and that ATP in them activates $P2X_7$ receptors that allow LY into the cytoplasmic and nuclear matrices. Furthermore, as described above endogenous ATP from IgGrRBCg+TPHPARIGL (SEQ ID. NO:1)+LY will be hydrolyzed by loading these ghosts with apyrase.) Uningested IgGrRBCg will be removed by lysis as described above, the peritoneal macrophages or J774 cells will be further incubated at 37° C. for varying time periods to allow processing of the TPHPARIGL. The macrophages or J774 cells then will be labeled with $^{51}Cr$ and incubated with various ratios of CTL0805B cells (e.g., 10–50 CTL0805B cells per target cell) for 4 hours at 37° C., at which time the medium from these cultures will be collected, sedimented to remove detached but unlysed cells, and assayed for $^{51}Cr$ release as a measure of cytotoxicity, as described (8). Positive controls should show that CTL0805B will lyse macrophages, wild type J774 cells, or J774-$P2X_7$ null cells that were pre-loaded incubated with high concentrations of TPHPARIGL peptide prior to incubating them with CTL0805B. CTL0805B should not lyse the following cells: 1. Macrophages or J774 cells treated with cytochalasin D to prevent ingestion of the IgGrRBCg+TPHPARIGL (SEQ ID. NO:1)+ATP or of the IgGrRBCg+TPHPARIGL (SEQ ID. NO:1). 2. J774-$P2X_7$ null cells incubated with IgGrRBCg+TPHPARIGL (SEQ ID. NO:1)+ATP or IgGrRBCg+TPHPARIGL (SEQ ID. NO:1). 3. Macrophages or J774 cells treated with Brefeldin A to prevent transport of TPHPARGL (SEQ ID. NO:1)-loaded Class I MHC proteins from the endoplasmic reticulum to the surface. 4. Macrophages or J774 cells incubated with IgGrRBCg+ATP and a scrambled peptide to which CTL0805B cells do not react. Anticipated results: CTL0805B will only kill syngeneic macrophages or wild type J774 cells that have processed IgGrRBCg+TPHPARIGL (SEQ ID. NO:1)+ATP.

Experimental plan: 2. Whether IgCrRBCg containing TPHPARIGL (SEQ ID. NO:1) and ATP, but not IgGrRBCg containing—TPHPARIGL (SEQ ID. NO:1) but lacking ATP, can be used to immunize naive mice to form CTL that lyse sygeneic macrophages or J774 cells loaded with the peptide.

Balb/c mice will be immunized weekly for 3–6 weeks intra-peritoneally, or subcutaneously in the neck or hind footpad with rRBCg or IgGrRBCg containing TPHPARIGL (SEQ ID. NO:1) with or without ATP. As a control, similar numbers of mice will be immunized with J774 cells incubated in TPHPARIGL (SEQ ID. NO:1)-containing buffer to load Class I MHC proteins with this peptide as described (8). For mice immunized subcutaneously, T-lymphocytes will be obtained from regional lymph nodes and spleen. For mice immunized intra-peritoneally T-lymphocytes will be obtained from spleen. Spleen and lymph node cells from immunized mice will be tested for induction of CTL against TPHPARIGL (SEQ ID. NO:1)-pulsed Balb/c macrophages (syngeneic), TPHPARIGL (SEQ ID. NO:1)-pulsed C57B1/6 macrophages (allogeneic), or J774 cells, as in 1. above, and for helper T-lymphocyte activity using $^3H$-thymidine incorporation or IL-2 production using X-irradiated lac-Z transfected Balb/c 3T3 cells (9).

In a second series of experiments Balb/c dendritic cells or marcrophages will be allowed to ingest IgGrRBCg containing TPHPARIGL with or without ATP. Uningested IgGrRBCg+TPHPARIGL (SEQ ID. NO:1) will be lysed, and these APCs will be administered to Balb/c mice weekly for 3–6 weeks intra-peritoneally or subcutaneously. The mice then will be sacrificed and their spleen and regional lymph node cells tested for CTL activity against TPHPARIGL (SEQ ID. NO:1)-pulsed J774 cells (as described in 8), and for helper T-lymphocytes using $^3H$-thymidine incorporation or IL-2 production using X-irradiated lac-Z transfected Balb/c 3T3 cells as stimulators (9).

Anticipated results: rRBCg+TPHPARIGL (SEQ ID. NO:1)+ATP, IgGrRBCg TPHPARIGEL (SEQ ID. NO:2)+ATP, or macrophages or dendritic cells that ingested IgGrRBCg TPHPARIGEL (SEQ ID. NO:2)+ATP will induce formation of CTLs while rRBCg+TPHPARIGEL (SEQ ID. NO:2), IgGrRBCg+TPHPARIGEL (SEQ ID. NO:2), or macrophages or dendtitic cells that ingested IgGrRBCg+TPHPARIGEL (SEQ ID. NO:2) will not. In contrast, all preparation will induce activation of helper T-lymphocytes.

Next, after obtaining positive results in the experiments described in 2 above, $P2X_7$-knock out mice will obtained and it will be determined whether they are incapable of mounting a helper or CTL response to IgGrRBCg+ TPHPARIGL (SEQ ID. NO:1) +ATP.

The mechanism by which APCs activate helper and cytotoxic lymphocytes to react to peptide antigens, including peptides with altered amino acid sequences from mutated tumor-cell proteins, is central to current immunotherapeutic approaches to cancer. The experiments herein will provide insight into the cellular mechanism by which apoptotic cells deliver antigenic peptides to Class I MHC of APCs and may uncover a novel and potentially clinically useful protocol for activating cytotoxic and helper T-lymphocytes.

REFERENCES

1. Mellman et al., Trends in Cell Biol. 8:231–237, 1998.
2. MacKenzie et al., Ann. N.Y. Acad. Sci. 868:716–729, 1999.
3. Mutini et al., J. Immunol. 163:1958–1965, 1999.
4. Steinberg et al., J. Biol. Chem. 262:8884–8888, 1987.
5. Coutinho-Silva et al., Am. J. Physiol. 276:C1139–1147, 1999.
6. Fratazzi et al., J. Immunol. 156:679–684, 1997.
7. Zambon et al., Cell Immunol. 156:458–467, 1994.
8. Buckner et al., Eur. J. Immunol. 27:2541–2548, 1997.
9. Lin et al., Cancer Res. 50:2808–2817, 1990.

What is claimed is:

1. A method of inducing immunity against an antigen in a subject having a disease associated with the presence of the antigen in the subject, which method comprises:
   a) contacting isolated antigen presenting cells (APCs) with antigen- and ATP-filled particles (Ag/ATP-filled particles) under conditions permitting phagocytosis of the particles by the APCs, wherein the particles are coated with a ligand for the APCs, such that the antigen is expressed on the surface of the APC (AG-APCs);
   b) incubating the Ag-APCs of step (a) with lymphocytes removed from the subject having the disease; and
   c) administering the incubated lymphocytes resulting from step (b) to the subject thereby inducing immunity against the antigen in the subject.

2. The method of claim 1, wherein the particles are type O red blood cell ghosts.

3. The method of claim 1, wherein the particles are liposomes.

4. The method of claim 1, wherein the ligand is selected from the group consisting of an immunoglobulin (IgG), complement component C3b, complement component C3bi, maleic anhydride, an oxidized lipid, a sugar, and a polyanion.

5. The method of claim 1, wherein the antigen presenting cells a re selected from the group consisting of dendritic cells, Langerhans cells, monocytes, mononuclear phagocytes, macrophages, Kupfer cells, microglial cells, osteoclasts, and bone marrow-derived leukocytes.

6. The method of claim 1, wherein the antigen is a purified antigen.

7. The method of claim 6, wherein the antigen is a cancer cell antigen, a bacterial antigen or a viral antigen.

8. The method of claim 1, wherein the antigen is derived from a crude cell extract.

9. The method of claim 8, wherein the antigen is a cancer cell antigen, a bacterial antigen or a viral antigen.

10. The method of claim 6, wherein the antigen is selected from the group consisting of a peptide, a carbohydrate, a lipid, a glycoprotein, a glycolipid and a lipoprotein.

11. The method of claim 1, wherein the Ag/ATP-filled particles further comprise at least one stimulatory cytokine.

12. The method of claim 11, wherein the cytokine is IL-0.12, G-CSF, IL-4, GM-CSF or interferon gamma.

13. The method of claim 1, wherein the immunity induced is against a bacterial or viral antigen.

14. The method of claim 1, wherein the immunity induced is against an antigen present in a cancerous tumor.

15. The method of claim 1, wherein the subject is afflicted with a bacterial- or a viral-mediated disease.

16. The method of claim 1, wherein the disease is cancer.

* * * * *